United States Patent [19]

Piselli et al.

[11] Patent Number: 5,495,013
[45] Date of Patent: Feb. 27, 1996

[54] PROCESS FOR THE PREPARATION OF DILTIAZEM

[75] Inventors: Fulvio L. Piselli; Piermarino Boschi; Claudio Navoni, all of Milan, Italy

[73] Assignee: Profarmaco Nobel S.r.l., Milan, Italy

[21] Appl. No.: 326,312

[22] Filed: Oct. 20, 1994

Related U.S. Application Data

[63] Continuation of Ser. No. 141,251, Oct. 21, 1993, abandoned.

[30] Foreign Application Priority Data

Oct. 23, 1992 [IT] Italy .................. MI92A2432

[51] Int. Cl.⁶ .................. C07D 281/10
[52] U.S. Cl. .................. 540/491
[58] Field of Search .................. 540/491

[56] References Cited

U.S. PATENT DOCUMENTS 4,902,684  2/1990  Floyd .................. 540/491

5,382,663  1/1995  Manghisi .................. 540/491

FOREIGN PATENT DOCUMENTS 92-10485  6/1992  WIPO .

*Primary Examiner*—Mark L. Berch
*Attorney, Agent, or Firm*—Bucknam and Archer

[57] ABSTRACT

A process for the preparation of Diltiazem of formula (I)

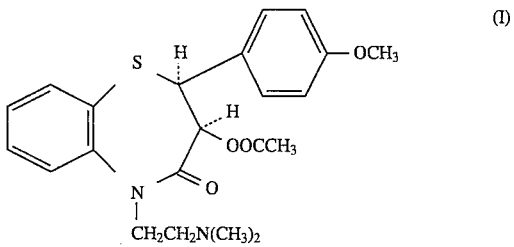

starting from the corresponding benzothiazepine and carried out throughout a 11 the steps in a single solvent.

3 Claims, No Drawings

PROCESS FOR THE PREPARATION OF DILTIAZEM

This is a continuation, of application Ser. No. 141,251, filed Oct. 21, 1993, ABN.

The present invention relates to a process for the preparation of (+)-cis-3-acetoxy-5-[2-(dimethylamino)ethyl] -2,3-dihydro-2- (4-methoxyphenyl) -1,5-benzothia-zepin-4 - (5H) -one of formula (I):

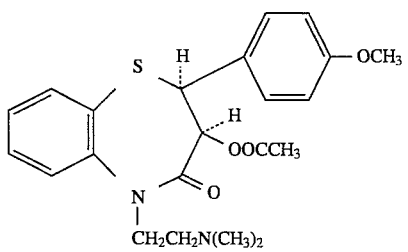

Said compound is also known under the international common name Diltiazem and is an important active principle having calcium-antagonist properties.

Nowadays, Diltiazem is used in the cardiovascular therapy, particularly in the treatment of angina pectoris.

The preparation of Diltiazem is known from 3,562,257 (Tanabe, 1971) starting from (+)-cis-3-hydroxy -2,3-dihydro-2-(4-methoxyphenyl) -1,5-benzothia-zepin -4-(5H)-one, of formula (II):

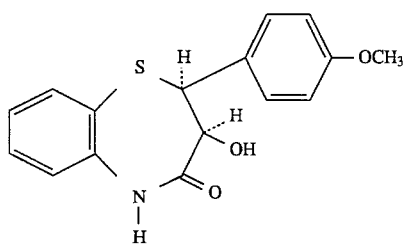

the preparation of which is disclosed in the same patent, by reaction with dimethylaminoethyl chloride of formula (III):

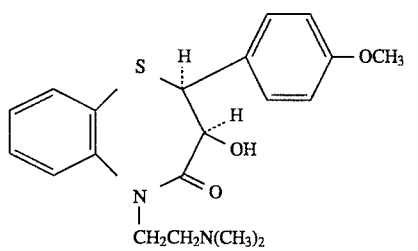

which is then transformed into compound (I). The reaction of (II) with (III) is carried out under critical conditions, since the alkylation of the thiazepine nitrogen takes place using very strong bases, such as sodium hydride, metal sodium or sodium amide in a solvent such as dimethylsulfoxide, dioxane, toluene or xylene.

Tanabe Patent teaches that the preferred conditions envisage the NaH/(CH$_3$)$_2$SO system.

Such a system is rather dangerous, in view of its potential explosiveness (Chem. Eng. News, 44 (15), 48 (1966)) and the severe environmental problems involved.

In a subsequent Patent (U.S. No. 4,438,035, 1984, corresponding to EP 0,081,234), Tanabe proposes another method in order to overcome the drawbacks of the preceding one. In fact, (II) and (III) are reacted in the presence of potassium hydroxide or carbonate in a solvent which can be acetone or lower alkyl acetate, preferably containing a small amount of water.

This method, even though overcoming some drawbacks of the previous process, still involves high costs both in economic and environmental terms.

In fact, the reaction takes place in heterogeneous phase and the solvent cannot be recovered since it is impossible to remove side-products and impurities. The product having the 3-hydroxy group free or acetylated is recovered and subsequently transformed into the final compound. In a communication to EPO, during the examination procedure, Tanabe states the N-alkylation of (II) does not take place when the reaction solvent is toluene, independently on how strong the used base (KOH and NaNH$_2$) is. In the same communication, it is moreover stated that sodium carbonate (even though in acetone) does not yield the desired result.

Now it has surprisingly been found that the reaction of (II) with (III) takes place in aromatic solvents in the presence of an alkali metal carbonate, preferably sodium carbonate. It should be noted that the latter allows to obtain a product which is substantially purer than the one obtained using potassium carbonate.

The process of the invention comprises the following steps: reacting (+)-cis-3-hydroxy-2,3-dihydro -2-(4-methoxyphenyl)-4-(5H)-one (II) with 2-dimethylaminoethyl chloride (III) in the presence of sodium carbonate, to give (+)-cis-3-hydroxy-5-[2-dimethylamino) ethyl]-2,3-dihydro-2- (4-methoxyphenyl) -4-(5H)-one (IV); acetylating compound (IV); recovering compound of formula (I) or possibly salifying it.

Examples of aromatic solvents are toluene, xylene, chlorobenzene, dichlorobenzene. Toluene and chlorobenzene are preferred. Toluene is particularly preferred.

The process of the present invention overcomes the drawbacks of the known technique as the solvent of the reaction of (II) with (III) is completely recovered in order to be recycled. A further advantage of the process is that the whole preparation cycle of compound (I) is effected in the aromatic solvent.

A preferred embodiment of the invention comprises reacting (II) with (III) in toluene, in the presence of sodium carbonate, to give (IV); treating the toluene solution of (IV) with an acetylation agent, preferably acetic anhydride, to obtain (I). At this time, Diltiazem can be recovered as the free base distilling toluene, which is subsequently purified according to conventional methods, or the Diltiazem toluene solution is treated with an acid to give the corresponding salt.

The salt precipitates directly from toluene and is recovered in a conventional way, by filtration, centrifugation, distillation of toluene, and the like. The salt is optionally recrystallized, if desired.

Then toluene is redistilled, recovering 70–80% of the pure solvent, which can be recycled in the subsequent cycle.

In another embodiment of the invention, compound of formula (III), which is usually used as the free base, is obtained starting from a salt thereof, generally the hydrochloride. According to the process of the invention, the recovery of (III) from its salt is carried out in toluene, in the presence of a strong aqueous base.

After decantation of the aqueous phase containing the inorganic salts, the N-alkylation reaction can be effected in the same reactor, without changing the solvent.

The process of the invention overcomes the problems for the recovery of the solvent involved in the known technique, moreover it has the advantage of obtaining Diltiazem, as the base or a salt, without isolating the reaction intermediates or changing the solvent, with evident advantages in terms of cost savings, plant simplification and security.

The following example further illustrates the invention.

Example a) Dimethylaminoethyl chloride (III)

1600 l of distilled toluene were charged into a 4600 l stainless steel reactor fitted with a stirrer, then 400 l of water and 250 kg of dimethylaminoethyl chloride hydrochloride were charged. The mixture was cooled with brine at 0°–10° C. and then 207 kg of 47% potassium hydroxide were charged. The reaction mixture was stirred for 15 minutes at 5°–10° C., after that it was left to stand, without stirring, for 30 minutes.

The aqueous phase was completely decanted in a tank. After checking the assay (w/v), the toluene phase contained 170 kg of (III), 91% molar yield.

b) (+)-cis-3-hydroxy-5-[2-dimethylamino)ethyl]-2,3-dihydro -2-(4-methoxyphenyl)-1,5-benzothiazepin-4-(5H)-one (II)

410 kg of anhydrous sodium carbonate and 275 kg of dry (+)-cis-3-hydroxy-2,3-dihydro-2-(4-methoxyphenyl)-1,5 -benzothiazepin-4-(5H)-one (II) were placed into the reactor of step a) , fitted with stirrer, temperature check system, Markusson water extractor and containing the dimethylaminoethyi chloride (III) toluene solution. The reaction mixture was refluxed for 5 hours and the progress of the reaction was checked by TLC. When the react ion was completed, the toluene solution was separated from the inorganic salts by centrifugation.

c) (+)-cis-3-acetoxy,5-[2-(dimethylamino)ethyl]-2,3-dihydro -2-( 4-methoxyphenyl)-1,5-benzothiazepin-4-(5H)-one (I)

The toluene solution from step b) was placed into the clean stainless reactor, followed by 1000 l of water. The mixture was heated to 60° C. for 1 hour, keeping the pH of the aqueous phase at about 8 with sodium hydroxide. The mixture was left to stand for 30 minutes, then the aqueous phase was separated. Subsequently, 400 kg of acetic anhydride were quickly added. The reaction was carried out for 10 hours at 60°–65° C. under stirring. When the reaction was completed, the mixture was cooled to a temperature below 20° C., then a separately prepared mixture was added, consisting of 700 l of water and 680 l of 30% sodium hydroxide aqueous solution, keeping stirring for 2 hours at 25° C. and pH about 5. At the end of the addit ion, pH reached a value of 8–9. Then 15 kg of sodium carbonate were added quickly, bringing the pH of the aqueous phase to about 10. The reaction mixture was stirred for 30 minutes at 20°–25° C., then the reactor was completely filled with water, the mixture was stirred for 10 minutes and left to stand for 30 minutes. After decantation and separation of the aqueous phase, the washings from the centrifugation of step b) were added and pH was adjusted to 7.0–7.4 with sodium hydroxide. After standing for 30 minutes, the aqueous phase was decanted and 800 l of water and 1l of acetic acid were added. After 15–30 minute stirring at 20°–25° C., the aqueous phase was decanted completely.

The toluene solution contained the title product in a 92% molar yield.

d) (+)-cis-3-acetoxy-5-[2-(dimethylamino)ethyl]-2,3-dihydro -2-(4-methoxyphenyl)-1,5-benzothiazepin-4-(5H)-one hydrochloride The toluene solution from step c) was placed into a 4000 l enamelled reactor, followed by 250 l of isopropanol. The mixture was stirred for 10 minutes, then left to stand for 30 minutes and the water content was checked ( lower than 0.50%). The reaction mixture was then treated with gas HCl, keeping temperature at 20°–25° C. and pH at 6. After complete precipitation, the mixture was centrifuged twice, washing each time the salts with 150 l of toluene, collecting the mother liquors.

350 kg of dry Diltiazem hydrochloride (85% yield on compound II) were obtained.

Crystallization mother liquors were distilled to recover toluene (about 70% recovery yield).

We claim:

1. A process for the preparation of (+)cis-3-acetoxy-5-2, 3-dihydro-2 -(4-methoxy-phenyl)-1,5-benzothiazepin-4-(5H)-one of formula (I):

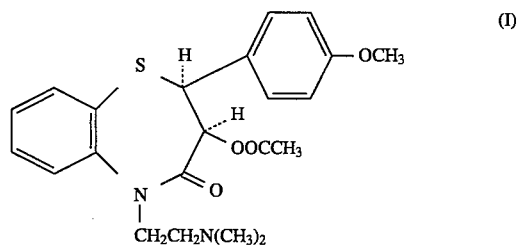

and a salt thereof, which consists of the following steps:

a) reacting under anhydrous conditions (+)-cis-3-hydroxy-2,3-dihydro-(4-methoxyphenyl)-1,5 -benzothiazepin-4-(5H)-one of fomula (II):

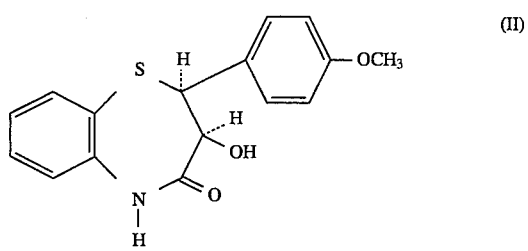

with 2-dimethylaminoethyl chloride of formula (III):

$(CH_3)_2N-CH_2CH_2-Cl$   (III)

in the presence of sodium carbonate, to give (+)-cis-3-hydroxy-5-2,3-dihydro-2-(4-methoxyphenyl) -1,5-benzothiazepin-4-(5H)-one of formula (IV):

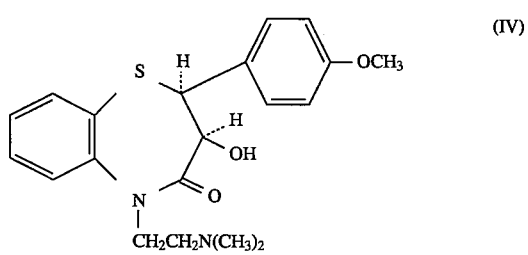

b) acetylating said compound of formula (IV);

c) recovering said compound (+)-cis-3-acetoxy-5-2,3-dihydro-2-(4-methoxyphenyl) 1,5-benzothiazepin-4-(5H)-one of formula (I) and when a salt thereof is desired, adding an acid to form the salt of said compound of formula I, wherein all said steps a) –c) are carried out in an aromatic solvent which is a member selected from the group consisting of toluene, xylene, chlorobenzene and dichlorobenzene.

2. The process according to claim 1, wherein said aromatic solvent is toluene.

3. The process according to claim 1, wherein after step c), the solvent is recovered and recycled to step a).

* * * * *